US012673910B2

(12) United States Patent
Kowalske et al.

(10) Patent No.: US 12,673,910 B2
(45) Date of Patent: Jul. 7, 2026

(54) PROCESS FOR PURIFICATION OF RECOVERED GLYCOL FROM CHEMICAL RECYCLING OF WASTE POLYESTER

(71) Applicant: Auriga Polymers, Inc., Charlotte, NC (US)

(72) Inventors: Michael Kowalske, Spartanburg, SC (US); Jason Smith, Boiling Springs, SC (US); Miguel Osornio, Spartanburg, SC (US); Matthiew Filanova, Greer, SC (US)

(73) Assignee: Auriga Polymers, Inc., Charlotte, NC (US)

( * ) Notice: Subject to any disclaimer, the term of this patent is extended or adjusted under 35 U.S.C. 154(b) by 688 days.

(21) Appl. No.: 18/020,571

(22) PCT Filed: Aug. 9, 2021

(86) PCT No.: PCT/US2021/045147
§ 371 (c)(1),
(2) Date: Feb. 9, 2023

(87) PCT Pub. No.: WO2022/035725
PCT Pub. Date: Feb. 17, 2022

(65) Prior Publication Data
US 2023/0312864 A1      Oct. 5, 2023

Related U.S. Application Data

(60) Provisional application No. 63/063,479, filed on Aug. 10, 2020.

(51) Int. Cl.
| | |
|---|---|
| *C07C 29/80* | (2006.01) |
| *C07C 31/20* | (2006.01) |
| *C08J 11/22* | (2006.01) |

(52) U.S. Cl.
CPC ............ *C07C 29/80* (2013.01); *C07C 31/202* (2013.01); *C08J 11/22* (2013.01); *C08J 2367/02* (2013.01)

(58) Field of Classification Search
CPC .......... C08J 11/22; C07C 29/80; C07C 29/86; C07C 31/202
See application file for complete search history.

(56) References Cited

U.S. PATENT DOCUMENTS

| | | | |
|---|---|---|---|
| 3,367,847 | A | 2/1968 | Pierson |
| 3,491,161 | A | 1/1970 | Pitts |

(Continued)

FOREIGN PATENT DOCUMENTS

| | | |
|---|---|---|
| JP | 02184644 H | 7/1990 |
| JP | 6-2687 B2 † | 1/1994 |

(Continued)

OTHER PUBLICATIONS

International Search Report corresponding to PCT/US2021/045147 mailed on Nov. 17, 2021.

*Primary Examiner* — Yate' K Cutliff
(74) *Attorney, Agent, or Firm* — Seth L. Hudson

(57) ABSTRACT

A process for purifying polyester-grade ethylene glycol from crude ethylene glycol containing at least a first component and a second component that have a boiling point below that of ethylene glycol that includes (a) providing a stream of crude ethylene glycol by depolymerizing polyethylene terephthalate in a chemical recycling process; (b) introducing the crude ethylene glycol stream into a first distillation column for distilling the first component and removing the first component from the process; (c) withdrawing a first stream from the lower portion of the first distillation column and feeding the first stream into a second distillation column for distilling the second component and removing the second component from the process; (d) withdrawing a second (Continued)

stream from the lower portion of the second distillation column and feeding the second stream into a third distillation column; and (e) recovering polyester-grade ethylene glycol from the third distillation column.

15 Claims, 1 Drawing Sheet

(56)                References Cited

U.S. PATENT DOCUMENTS

| | | | |
|---|---|---|---|
| 4,028,195 | A | 6/1977 | Becker et al. |
| 4,519,875 | A | 5/1985 | Becker et al. |
| 4,830,712 | A | 5/1989 | Crandall et al. |
| 5,051,528 | A | 9/1991 | Naujokas et al. |
| 5,298,530 | A | 3/1994 | Gamble et al. |
| 5,391,263 | A | 2/1995 | Hepner et al. |
| 5,414,022 | A | 5/1995 | Toot, Jr. et al. |
| 5,576,456 | A | 11/1996 | Gamble et al. |
| 5,672,780 | A | 9/1997 | Gamble et al. |
| 5,770,778 | A | 6/1998 | Naujokas |
| 6,472,557 | B1 | 10/2002 | Pell, Jr. et al. |
| 6,706,843 | B1 † | 3/2004 | Ishihara |
| 7,173,150 | B2 | 2/2007 | Yazaki et al. |
| 12,134,592 | B2 | 11/2024 | De Haan et al. |
| 2019/0202764 | A1 | 7/2019 | Fischer et al. |
| 2020/0216377 | A1 * | 7/2020 | Jackson .................. C07C 29/80 |
| 2022/0009864 | A1 | 1/2022 | De Haan et al. |

FOREIGN PATENT DOCUMENTS

| | | | | |
|---|---|---|---|---|
| JP | 2004131394 | A | 4/2004 | |
| JP | 2003135902 | A | 10/2006 | |
| JP | 2002308804 | B2 | 5/2010 | |
| JP | 6270100 | B2 † | 1/2018 | |
| KR | 100648397 | B1 | 6/2002 | |
| WO | WO-9803459 | A1 * | 1/1998 | ............. C07C 51/09 |
| WO | 2011043515 | | 4/2011 | |
| WO | WO-2020002999 | A2 * | 1/2020 | .............. C08J 11/24 |

* cited by examiner
† cited by third party

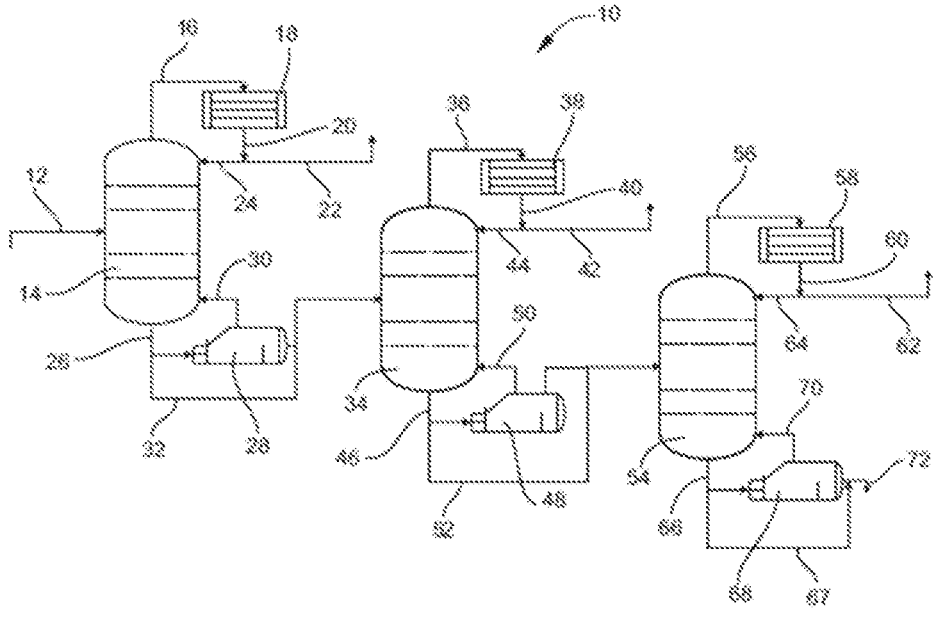

PROCESS FOR PURIFICATION OF RECOVERED GLYCOL FROM CHEMICAL RECYCLING OF WASTE POLYESTER

FIELD OF THE INVENTION

The present invention relates generally to a process for recovering polyester-grade ethylene glycol from a crude ethylene glycol product stream produced from colored post-consumer recycled resin and more generally relates to a process for recovering at least 99.9% purity pure ethylene glycol from a crude ethylene glycol product stream produced from the depolymerization of a colored post-consumer recycled resin, such as polyethylene terephthalate (PET), by a chemical recycling process.

BACKGROUND OF THE INVENTION

Polyethylene terephthalate, more commonly known as PET in the packaging industry, is an indispensable material with immense applications. PET has excellent physical and chemical properties, resulting in its widespread use in single and multiple use products such as food and beverage containers and the like.

PET is a polycrystalline polyester formed from the esterification of terephthalic acid (TPA) with ethylene glycol (EG) or from the transesterification of dimethyl terephthalate (DMT) with ethylene glycol (EG). Synthesis of PET from either process involves two reaction steps. The first step is the formation of an intermediate monomer bis(2-hydroxyethyl) terephthalate (BHET) with the release of a small molecule, which is either water (esterification of TPA with EG) or methanol (transesterification of DMT with EG). The second is the polycondensation of BHET to produce PET in melt phase with the release of EG under high vacuum.

In an effort to conserve raw petrochemical products and energy, several methods have been developed for the recycling of PET. These PET recycling methods can be categorized into four groups, namely, primary, secondary, tertiary (chemical) and quaternary recycling. Primary recycling, also known as re-extrusion, refers to "in-plant" recycling of scrap materials that have similar features to the original products and requires uncontaminated scrap. Secondary recycling, also known as mechanical recycling, involves the separation of the polymer from its contaminants and reprocessing it to granules by sorting and separation of wastes, removal of contaminants, reduction of size by crushing and grinding, extrusion by heat, and reforming. Tertiary or chemical recycling, involves the transformation of the PET polymer chain, such as depolymerization, i.e., breaking the ester bond and reducing the polymer to its monomer components. Quaternary recycling is the recovery of energy content from the waste by incineration.

Recycling bottles formed of PET to form bottles composed of PET is preferably due to its higher added value. Such recycling is commonly known as "bottle to bottle recycling," instead of recycling bottles formed of PET to fiber grade PET to produce apparel. In order to engage in bottle to bottle recycling, the recycled PET has to satisfy the requirements for bottle processing (glass transition and melting temperatures, melt viscosity, melt stiffness, rate of crystallization, and thermal stability) as well as approval for food contact (decontamination, color, and haze). Due to the required high decontamination levels of recycled PET for food-packaging applications, the bottle to bottle recycling should be a chemical recycling process involving depolymerization. Depolymerization may be performed by hydrolysis, glycolysis, or methanolysis, thus forming monomers and/or oligomers. Chemical recycling is the only acceptable process according to the principles of sustainable development, because it leads to the formation of raw materials (monomers) from which the PET was made.

The decontamination capability of the chemical recycling process is an important objective function to recycle PET for food packaging applications. The removal of various contaminants needs to be accounted for during the process. It is an object of the present invention to provide a process to purify ethylene glycol and recover purified ethylene glycol that is polyester-grade. Another object of the process is to purify ethylene glycol and recover purified ethylene glycol that is polyester-grade from a crude ethylene glycol product stream containing contaminants, including contaminants formed during the chemical recycling process without introducing additional components, such as catalysts, to the process.

Various methods have been disclosed in the literature for depolymerization of post-consumer polyesters into their component monomers, such as ethylene glycol and terephthalic acid, naphthalene dicarboxylic acid or their derivatives, so they can be reused.

For example, U.S. Pat. No. 3,367,847 discloses a process for purifying ethylene glycol recovered from a process for making films and fibers of linear polyesters made from ethylene glycol and terephthalic acid. In the process, sodium salts of terephthalic acid are first removed from the ethylene glycol, and then the ethylene glycol is subjected to fractional distillation to remove the high and low boiling point impurities. The distilled ethylene glycol is then treated with activated carbon to remove impurities that adversely affect the ultra-violet light transmission.

U.S. Pat. No. 3,491,161 discloses the treatment of ethylene glycol contaminated with dimethyl terephthalate and other esters and impurities with a stoichiometric amount of ammonia for converting the ester impurities to corresponding amides and alcohols and distilling the reaction mixture to recover ethylene glycol.

U.S. Pat. No. 4,028,195 discloses recovery of ethylene glycol or 1,2-propylene glycol admixed with the lower alkanoate monoester of the glycol and an azeotroping agent from a previous distillation. The glycol is introduced into a fractional distillation zone containing at least one aqueous acetic acid and an aqueous formic acid to suppress the formation of an ortho ester and the purified glycol is recovered from the lower portion of the zone.

U.S. Pat. No. 4,519,875 discloses the purification of ethylene glycol for fiber-grade applications by removal of the residual ethylene carbonate from which the glycol was derived. The effluent from a reactor in which the ethylene carbonate is hydrolyzed is distilled to produce a lower-boiling fraction comprising substantially ethylene glycol and water and a higher-boiling fraction comprising substantially ethylene glycol, higher glycols, and a catalyst. The higher-boiling fraction is recirculated to reflux against the lower-boiling product completing the hydrolysis of unreacted ethylene carbonate and reducing the ethylene carbonate content of the ethylene glycol to very low levels suitable for fiber-grade applications.

U.S. Pat. No. 4,830,712 discloses a process for recovering ethylene glycol from crude ethylene glycol containing at least one component which has a normal boiling point below that of ethylene glycol, and which can form a UV absorber in the presence of ethylene glycol. The purification process includes a fractional distillation zone having an upper portion, a lower portion and an intermediate portion. A crude ethylene glycol stream at a determined pH of less than about 7.5 is maintained within the intermediate portion of the fractional distillation zone. A diluent is included at a concentration sufficient to reduce the formation of UV absorber in the intermediate portion. The ethylene glycol is withdrawn from the lower portion of the fractional distillation zone.

U.S. Pat. No. 5,051,528 discloses a method of recovering ethylene glycol and dimethyl terephthalate from scrap polyethylene terephthalate resins by dissolving the scrap in oligomers of the same monomers and passing methanol through the solution.

U.S. Pat. No. 5,298,530 discloses a process of recovering components such as ethylene glycol and dimethyl terephthalate from scrap polyester. The process steps are: (a) introducing oligomers of ethylene glycol and terephthalate acid or dimethyl terephthalate to a first vessel and heating the oligomers; (b) introducing scrap polyester to the first vessel and forming a startup melt with the oligomers; (c) transferring melt from the first vessel to a second vessel; (d) passing super-heated methanol through the melt in the second vessel to form a final melt comprising low molecular weight polyesters and monomers; (e) transferring final melt from the second vessel to the first vessel; and (f) recovering components from the second vessel.

U.S. Pat. No. 5,391,263 discloses the separation of ethylene glycol and diethylene glycol from dimethyl terephthalate is by distillation and using methyl benzoate or the methyl ester of p-toluic acid as an azeotropic agent.

U.S. Pat. No. 5,414,022 discloses a process and optimal conditions for depolymerizing polyester into its components and separating the components using apparatus that includes a dissolver for receiving polyester, a reactor for depolymerizing polyester into components, and a rectifier for separating polyester components. The process includes (a) adding polyester to the dissolver and combining it with melt from the reactor and liquid from the rectifier to reduce the chain length of the polyester; (b) transferring reduced chain length polyester from the dissolver to the reactor; (c) passing super-heated methanol through the reactor to depolymerize polyester into its constituent monomers; (d) transferring depolymerization products from the reactor to the rectifier; and (e) separating the depolymerization products in the rectifier into a vapor phase containing component monomers and a liquid phase containing higher molecular weight materials.

U.S. Pat. No. 5,576,456 discloses a process for the depolymerization of polyethylene terephthalate into component monomers using a reactor in which the polyethylene terephthalate is a discontinuous phase which contacts a continuous phase of superheated methanol vapor.

U.S. Pat. No. 5,672,780 discloses a process for removing dimethyl terephthalate contaminants from ethylene glycol. The process comprises distilling ethylene glycol in the presence of an ester exchange catalyst to cause a reaction between ethylene glycol and dimethyl terephthalate to form compounds that are less volatile than either ethylene glycol or dimethyl terephthalate, such as bis(hydroxyethyl) terephthalate.

U.S. Pat. No. 5,770,778 discloses a process for purifying ethylene glycol recovered from scrap polyester by contacting the recovered ethylene glycol with a first adsorbent that has a high affinity for polar contaminants and a second adsorbent that has a high affinity for non-polar contaminants.

U.S. Pat. No. 6,472,557 discloses producing high quality TPA suitable for PET feedstock material from recycled polyester. The process includes the steps of depolymerizing the polyester to form DMT; separating the DMT from secondary materials; and hydrolyzing the DMT to form TPA.

U.S. Pat. No. 6,706,843 discloses separation and recovery of dimethyl terephthalate and ethylene glycol from polyester waste containing foreign materials. The polyester waste is treated in ethylene glycol containing a polyester depolymerization catalyst. A solid foreign material fraction is floated on the surface of the resultant reaction solution and removed, and the residual solid foreign material fraction is removed from the remaining solution fraction. The remaining solution fraction is distilled and concentrated, and the distilled ethylene glycol is recovered. A transesterification reaction catalyst and methanol are mixed into the distillation residue. The resultant reaction mixture is recrystallized and subjected to centrifugal separation to separate the reaction mixture into the DMT cake and a mixture solution, and then the cake is distilled whereby high-purity DMT is recovered. The residual mixture solution is subjected to distillation treatment for recovery of the methanol, and the distillation residue is distilled to recover EG.

BRIEF SUMMARY OF THE INVENTION

According to an embodiment of the present invention, a process for purifying polyester-grade ethylene glycol from crude ethylene glycol containing at least a first component and a second component that have a boiling point below that of ethylene glycol that includes (a) providing a stream of crude ethylene glycol by depolymerizing polyethylene terephthalate in a chemical recycling process; (b) introducing the crude ethylene glycol stream into a first distillation column for distilling the first component and removing the first component from the process; (c) withdrawing a first stream from the lower portion of the first distillation column and feeding the first stream into a second distillation column for distilling the second component and removing the second component from the process; (d) withdrawing a second stream from the lower portion of the second distillation column and feeding the second stream into a third distillation column; and (e) recovering polyester-grade ethylene glycol from the third distillation column.

According to another embodiment of the present invention, the process for purifying polyester-grade ethylene glycol from crude ethylene glycol includes methanol as the first component.

According to yet another embodiment of the present invention, the process for purifying polyester-grade ethylene glycol from crude ethylene glycol includes water as the second component.

According to yet another embodiment of the present invention, the process for purifying polyester-grade ethylene glycol from crude ethylene glycol wherein the purity of the ethylene glycol is 99.9%.

According to yet another embodiment of the present invention, the process for purifying polyester-grade ethylene glycol from crude ethylene glycol wherein the purity of the methanol is 99.9%.

According to yet another embodiment of the present invention, the process for purifying polyester-grade ethylene glycol from crude ethylene glycol wherein the polyester-grade ethylene glycol contains less than 0.01 wt % chain terminators.

According to yet another embodiment of the present invention, the process for purifying polyester-grade ethylene glycol from crude ethylene glycol includes partial condensers.

According to yet another embodiment of the present invention, the process for purifying polyester-grade ethylene glycol from crude ethylene glycol wherein the first distillation column operates at a temperature of less than 56° C. at a pressure of 110 mm Hg.

According to yet another embodiment of the present invention, the process for purifying polyester-grade ethylene glycol from crude ethylene glycol wherein the second distillation column operates at a temperature range of greater than 56° C. to 196° C., and a pressure of 110 mm Hg.

According to yet another embodiment of the present invention, the process for purifying polyester-grade ethylene glycol from crude ethylene glycol wherein the third distillation column operates at a temperature range of greater or equal to 197° C. to less than 202° C., and a pressure of 110 mm Hg.

According to yet another embodiment of the present invention, the process for purifying polyester-grade ethylene glycol from crude ethylene glycol wherein no additional components, such as catalysts, are introduced into the process.

According to yet another embodiment of the present invention, a process for purifying polyester-grade ethylene glycol from crude ethylene glycol includes (1) providing crude ethylene glycol from a process for the depolymerization of polyethylene terephthalate (PET) to form a terephthalate; (2) admixing the polyethylene terephthalate (PET) with a first solvent that is methanol to yield a first mixture; (3) adding a glycoxide to the first mixture; (4) adding a second solvent that is methanol; (4) admixing; (5) evaporating or distilling crude ethylene glycol from the terephthalate; (6) introducing the crude ethylene glycol stream into a first distillation column for distilling the first component and removing the first component from the process; (7) withdrawing a first stream from the lower portion of the first distillation column and feeding the first stream into a second distillation column for distilling the second component and removing the second component from the process; (8) withdrawing a second stream from the lower portion of the second distillation column and feeding the second stream into a third distillation column; and (9) recovering polyester-grade ethylene glycol from the third distillation column.

According to yet another embodiment of the present invention, the process for purifying polyester-grade ethylene glycol from crude ethylene glycol includes a crude ethylene glycol containing one or more of the following: methanol, ethylene glycol, water, diethylene glycol, cyclohexane dimethanol (CHDM), BHET, bis(2-hydroxy methyl) isophthalate (BHEI), Methyl 4-formylbenzoate, 2-Methoxyethanol, 2-butoxyethanol, and 2-(2-ethoxyethoxy)—thanol, dyes and pigments.

BRIEF DESCRIPTION OF THE DRAWINGS

The present invention is illustrated and described herein with reference to the various drawings, in which like reference numbers denote like method steps and/or system components, respectively, and in which:

FIG. 1 is a schematic diagram illustrating the process of the present invention.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

It is to be understood that the ranges and limits mentioned herein include all ranges located within the prescribed limits (i.e., subranges). For instance, a range from about 100 to about 200 also includes ranges from 110 to 150, 170 to 190, 153 to 162, and 145.3 to 149.6. Further, a limit of up to about 7 also includes a limit of up to about 5, up to 3, and up to about 4.5, as well as ranges within the limit, such as from about 1 to about 5, and from about 3.2 to about 6.5 as examples.

The present invention is directed to a process for purifying and recovering purified ethylene glycol that is polyester-grade from crude ethylene glycol, resulting from a chemical recycling process. The resultant polyester-grade ethylene glycol produced from the present invention is obtained from polyester waste, which contains polyethylene terephthalate as the major component along with foreign components and contaminants. Polyethylene terephthalate may be depolymerized in a chemical recycling process by admixing the polyethylene terephthalate with a mixture comprising methanol and a catalyst, resulting in the recovery of dimethyl terephthalate and crude ethylene glycol. The crude ethylene glycol may be produced in accordance with the process contained in U.S. Patent Publication No. 2019/0390035 titled "Terephthalic Acid Esters Formation," which also discloses the use of catalysts, such as alkoxide, sodium methoxide, sodium glycoxide, and any combinations thereof.

During the depolymerization process, the reactions with the catalyst introduces additional contaminants into the crude ethylene glycol that must be removed to recover polyester-grade ethylene glycol. In accordance with the present invention, a process is provided for recovering polyester-grade ethylene glycol from crude ethylene glycol, when the crude ethylene glycol contains contaminants, some of which are a result of the catalyst used in the depolymerization process. In accordance with the present invention, a process is provided for recovering polyester-grade ethylene glycol from crude ethylene glycol that does not include the addition of components in the system for purification, such as catalysts. In accordance with the present invention, a process is provided for recovering >99.9 wt % polyester-grade ethylene glycol from crude ethylene glycol and <0.01 wt % chain terminators, wherein the crude ethylene glycol contains contaminants that are a result of the catalyst used in the depolymerization process.

The term chain terminator means any monoacid/monoester species that is capable of successful reaction with the diol/diols in the formulation and persists or remains in the polymer matrix after isolation of the polymer (for mono-substituted acid or ester based species) or any substance with a single alcohol functionality that is capable of successful reaction with the diacid/diesters in the formulation and persists or remains in the polymer matrix after isolation of said polymer (for mono-substituted alcohol-based species).

Referring now specifically to the drawings, a process is illustrated in FIG. 1 and is shown generally at reference numeral 10 for recovering polyester-grade ethylene glycol from crude ethylene glycol. The process 10 involves purifying crude ethylene glycol produced from the depolymerization of post-consumer recycled resin, including colored post-consumer recycled resin, such as PET. The crude ethylene glycol is obtained by a chemical recycling process for depolymerizing the resin or PET. There are three main methods in PET chemical recycling depending on the added hydroxyl bearing molecule: glycol for glycolysis, methanol for methanolysis, and water for hydrolysis. These methods are described in more detail below:

Hydrolysis:

Hydrolysis involves the depolymerization of PET to terephthalic acid (TPA) and ethylene glycol by the addition of water in acidic, alkaline or neutral environment. The hydrolysis product is optionally used to produce virgin PET, or is optionally converted to more expensive chemicals like oxalic acid. Concentrated sulfuric acid is usually used for acid hydrolysis, caustic soda for alkaline hydrolysis, and water or steam for neutral hydrolysis. Hydrolysis is slow compared to methanolysis and glycolysis, because among the three depolymerizing agents (i.e. water, methanol, ethylene glycol), water is the weakest nucleophile. It also always uses high temperatures or high pressures or a combination thereof. Another disadvantage of hydrolysis is the difficulty of recovery of the TPA monomer, which requires numerous steps in order to reach the required purity.

Methanolysis:

Methanolysis is the depolymerization of PET to dimethyl terephthalate (DMT) and ethylene glycol (EG) by methanol.

Glycolysis:

Glycolysis is carried out using ethylene glycol to produce bis(2-hydroxyethyl) terephthalate (BHET) and other PET glycolyzates, which can be used to manufacture unsaturated resins, polyurethane foams, copolyesters, acrylic coatings and hydrophobic dystuffs. The BHET produced through glycolysis can be added with fresh BHET and the mixture can be used in any of the two PET production (DMT-based or TPA-based) lines. Besides its flexibility, glyclolysis is the simplest, oldest, and least capital-intensive process. Because of these reasons, much attention has been devoted to the glycolysis of PET. Numerous works have been published about PET glycolysis, wherein the reaction has been conducted in a wide range of temperature and time. Studies on the kinetics of PET glycolysis have shown that glycolysis without a catalyst (such as metal salts, zeolites, or ionic liquids) is very slow and complete depolymerization of PET to BHET cannot be achieved.

The crude EG stream 12 introduced into the process of the present invention may be produced by any PET chemical recycling process, but preferably either methanolysis or glycolysis. In the present examples, the crude EG feed stream 12 was produced from the process contained in U.S. Patent Publication No. 2019/0390035 titled "Terephthalic Acid Esters Formation." The process disclosed in this patent application produces a crude EG feed stream 12 that may comprise the following components in Table 1a:

TABLE 1a

| Component | PPM |
|---|---|
| Methanol | 860,554 |
| Ethylene Glycol | 111,494 |
| Diethylene Glycol | 6,181 |
| CHDM | 2,289 |
| Water | 5,838 |
| Triethylene Glycol | 26 |
| Dimethyl Terephthalate | 18 |
| Dimethyl Isophthalate | 82 |
| BHET/BHEI | 2,979 |
| Methyl 4-formylbenzoate | 291 |
| NaMMT (Sodium Monomethyl Terephthalate) | 661 |
| PET coloring | 8,706 |
| 2-Methoxyethanol | 199 |
| 1,4-Dioxane | 1 |
| 2-Methyl-1,3-Dioxolane | 1 |
| Sodium Sulfate | 22 |
| 1,4-Butanediol | 22 |
| 1,2-Propylene Glycol | 12 |
| Neopentyl Glycol | 327 |
| 1,5-Hexanediol | 4 |
| 2,3-Butanediol | 8 |
| 2,2-Dimethyl-1,3-Butanediol | 4 |
| 1,3-Cyclobutanediol2,2,4, 4-tetramethyl | 180 |
| Acetic Acid, hydroxy, ethyl ester | 2 |
| Diethyl Phthalate | 2 |
| Ethanel,1'-oxybis[2-methoxy | 17 |
| 2-Butoxyethanol | 3 |
| 1-Propanol, 2-Ethoxy | 2 |
| 2-(2-Methoxyethoxy)-Ethanol | 52 |
| Ethanedioic Acid, Dimethylester | 17 |
| 1-Ethoxy-1-Methoxy-Ethane | 3 |
| 2-Decanol | 2 |

Additionally, the crude EG stream 12 may additionally include the components listed below in Table 1b:

TABLE 1b

| Component |
|---|
| 1-Octanol |
| 2-Propanol, 1-propoxy- |
| Diethylene glycol monododecyl ether |
| Triethylene glycol monododecyl ether |
| Cyclohexanemethanol, 4-methylene |
| Acetic acid |
| 2-Propenoic acid, 3-phenyl-, methyl ester |
| Hexanedecanoic acid, methyl ester |
| Methyl stearate |
| 11-Octadecenoic acid, methyl ester |
| Benzoic acid, 4-methyl-, methyl ester |
| Benzoic acid, 4-ethyl-, methyl ester |
| Benzoic acid, 4-(1,3-dioxolan-2-yl)-, methyl |
| 2-Cyclopentene-1,2-dicarboxylic acid, 3-methyl |
| Hexanedioic acid, dimethyl ester |
| 1,4-Cyclohexanedicarboxylic acid, dimethyl |
| 1,3-Dioxolane Acetic acid, hydroxy-, methyl ester |
| Acetic acid, hydroxy-, methyl ester |
| Pyrazine |
| Pyrazine, methyl |

As illustrated in FIG. 1, the crude EG feed stream 12 is introduced into a first distillation column 14, designed to separate the methanol (MeOH) from the crude EG product stream 12. Depending upon the operation of the first distillation column 14, the crude EG feed stream 12 may be vaporous, liquid, or a combination thereof. Preferably the temperature of the EG feed stream 12 is between about 20° C. to about 100° C., and more preferably about 25° C. to about 95° C. The EG feed stream 12 is illustrated as one stream in FIG. 1, but the EG feed stream 12 can be formed by two or more separate streams with different temperatures and flow rates. For example when an EG feed stream is formed by a first stream and a second stream, the first stream may have a temperature between about 20° C. to about 35° C. and a mass flow rate of between about 5,000 kg/hr to about 8,000 kg/hr, and the second stream may have a temperature between about 80° C. to about 100° C. and a mass flow rate of between about 6,000 kg/hr to about 9,000 kg/hr.

The first distillation column 14 is generally a cylindrical column with one or more separation stages and fitted with trays, structured packing, or a combination of trays and structured packing. The first distillation column 14 separates the higher boiling materials from the lower boiling methanol in the product stream. During operation, the lowest boiling point materials in the crude EG feed stream 12, principally comprising methanol and water, are removed through the first distillation gaseous stream 16 from the top of the first distillation column 14. The methanol removed from the first distillation column 14 has 99.9% purity, at least.

The operating temperature of the first distillation column 14 is preferably less than 56° C. at 110 mm Hg. Operation of the first distillation column 14 below 56° C. at 110 mm Hg allows for the distillation of methanol, while allowing ethylene glycol and the heavies to be removed from the bottom of the first distillation column 14. The temperature may be adjusted depending upon the components in the crude EG feed stream 12 introduced into the first distillation column 14 to prevent thermal decomposition of heavies and other components intended to be removed from the bottom of the first distillation column 44.

The first distillation column gaseous stream 16 is cooled in a first partial condenser 18 to partially condense most of the methanol. A stream 20 of purified methanol is withdrawn from the partial condenser 18, wherein most of the purified methanol leaves the process 10 through stream 22. Stream 22 has a temperature of between about 40° C. to about 65° C. and a mass flow rate of between about 11,000 kg/hr to about 13,000 kg/hr. A portion of the stream 20 containing the purified methanol is recirculated to the top of the first distillation column 14, preferably at a point above the location where stream 30 is introduced, through a methanol reflux stream 24. The temperature of the methanol reflux stream 24 is less than the temperature within the first distillation column 14. The reintroduction of the methanol reflux stream 24 to the top of the distillation column 14 allows for additional purification and increases the level of purity of the first distillation column gaseous stream 16 and efficiency of the first distillation column 14.

The higher boiling material components, principally comprising ethylene glycol, water, and heavies, exit the first distillation column 14 through the bottom in a tail stream 26. The heavies may include diethylene glycol, cyclohexanedimethanol (CHDM), dyes and pigments, and bis 2-hydroxyethyl terephthalate (BHET)/bis(2-hydroxy ethyl)isophthalate (BHEI) mixed monomer. A first reboiler 28 is provided at the bottom of the first distillation column 14. A portion of the tail stream 26, stream 27, is introduced into the first reboiler 28 to provide heat energy to vaporize the components of stream 27 for reintroduction into the first distillation column 14 by stream 30 and the remaining portion of tail stream 26 is fed into a second distillation column 34. The tail stream 26 preferably has a temperature between about 135° C. to about 155° C. and a mass flow rate of between about 1,000 kg/hr to about 2,500 kg/hr.

The tail stream 26 principally contains ethylene glycol, water, and heavies that enter the second distillation column 34, intended to separate the higher boiling materials, from the lower boiling materials, and removes the lower boiling materials from the top of the second distillation column 34 through the second distillation column gaseous stream 36. The second distillation column 34 is generally a cylindrical column with one or more separation stages and fitted with trays, structured packing, or a combination of trays and structured packing.

The operating temperature of the second distillation column 34 is preferably between about 56° C. to about 196° C. at 110 mm Hg. Operation of the second distillation column 34 within this temperature range allows for the distillation of water and other components having a boiling point within this range, while allowing ethylene glycol and the heavies to be removed from the bottom of the second distillation column 34. The temperature may be adjusted depending upon the components in the tail stream 26 fed into the second distillation column 34 to prevent thermal decomposition of heavies and other components intended to be removed from the bottom of the second distillation column 34.

The second distillation column gaseous stream 36 is cooled in a second partial condenser 38 to partially condense most of the water. A stream 40 principally containing purified water, methanol, and a small percentage of ethylene glycol is withdrawn from the second partial condenser 38, wherein most of the purified water leaves the process 10 through stream 42 at a temperature of between about 75° C. to about 95° C. and a mass flow rate of between about 80 kg/hr to about 100 kg/hr. A portion of the stream 40 is recirculated to the top of the second distillation column 34, preferably at a point above the location where the stream 50 is introduced, through a water reflux stream 44. The temperature of the water reflux stream 44 is less than the temperature within the second distillation column 34.

The higher boiling materials, principally comprising ethylene glycol, diethylene glycol, and heavies, such as CHDM, dyes and pigments, and BHET/BHEI, exit the bottom of the second distillation column 34 in a tail stream 46. A portion of the tail stream 46, stream 52, is introduced to a second reboiler 48 to provide heat energy to vaporize the components of the stream 52 for reintroduced into the second distillation column 34 by stream 50. The remaining portion of tail stream 46 is fed into the third distillation column 54. Tail stream 46 has a temperature between about 145° C. to about 160° C. and a mass flow rate between about 1,000 kg/hr to about 2,500 kg/hr.

The tail stream 46 principally comprises ethylene glycol, diethylene glycol, PET coloring, BHET/BHEI, and other heavies enter the third distillation column 54 intended to purify and separate the ethylene glycol from the other components of the tail stream 46, and remove the ethylene glycol from the top of the third distillation column 54 though the third distillation column gaseous stream 56. The third distillation column 54 is generally a cylindrical column with one or more separation stages and fitted with trays, structured packing, or a combination of trays and structured packing.

The operating temperature of the third distillation column 54 is preferably greater than or equal to 197° C. and less than 202° C. at 110 mm Hg. Operation of the third distillation column 54 within this temperature range allows for the distillation of ethylene glycol, while allowing the heavies to be removed from the bottom of the third distillation column 54 and removed from the process 10. The temperature may be adjusted depending upon the components in the tail stream 46 fed into the third distillation column 54 to prevent thermal decomposition of heavies and other components intended to be removed from the bottom of the third distillation column 54.

The third distillation column gaseous stream 56 contains purified ethylene glycol of >99.9 wt % that is a polyester-grade ethylene glycol and <0.01 wt % chain terminators. The chain terminators contained within the purified ethylene glycol contains less than or equal to 30 ppm chain terminators. The chain terminators found within the crude EG stream 12 may be Methyl 4-formylbenzoate, 2-Methoxyethanol, 2-Butoxyethanol, and 2-(2-Methoxyethoxy)-Ethanol, as shown in Table 1a and 1b.

The third distillation column gaseous stream 56 is cooled in a third partial condenser 58 to partially condense most of the ethylene glycol. A cooled stream 60 of ethylene glycol is withdrawn from the third partial condenser 58, wherein most of the purified ethylene glycol leaves the process 10 through stream 62. Stream 62 preferably has a temperature between about 120° C. to about 150° C. and a mass flow rate of between about 1,000 kg/hr to about 2,000 kg/hr. A portion of the cooled stream 60 is recirculated to the top of the third distillation column 54, preferably at a point above the location where the stream 70 is introduced, through an ethylene glycol reflux stream 64. The temperature of the ethylene glycol reflux stream 64 is less than the temperature within the third distillation column 14.

The higher boiling materials, principally comprising ethylene glycol bottoms, consisting of ethylene glycol, diethylene glycol, and heavies, such as CHDM, dyes and pigments, Methyl 4-formylbenzoate, and BHET/BHEI exit the bottom of the third distillation column 54 in a third tail stream 66. A portion of the third tail stream 66, stream 67, is introduced to a third reboiler 68 to provide heat energy to vaporize the components of the stream 67 for reintroduced to the third distillation column 54 by stream 70. The remaining components consisting of ethylene glycol bottoms and heavies are discharged as waste and exit the process 10 through stream 72. Stream 72 preferably has a temperature between about 160° C. to about 180° C. and a mass flow rate of between about 250 kg/hr to about 450 kg/hr.

The process 10 of the present invention contains a first distillation column 14, a second distillation column 34, and a third distillation column 54 in series. No additional components are introduced into the process 10, such as a catalyst, to purify and recover purified ethylene glycol that is polyester-grade.

Polyester-grade ethylene glycol means a high purity ethylene glycol suitable for use in the production of polyester, such as PET and specifically PET bottles.

EXAMPLES

The following examples are provided to illustrate the present invention. The examples are not intended to limit the scope of the present invention and they should not be so interpreted.

Example 1

Example 1 is based upon lab conditions and not run at a commercial scale. The crude EG used in the crude EG feed stream was produced in accordance with the process contained in U.S. Patent Publication No. 2019/0390035 titled "Terephthalic Acid Esters Formation" and incorporated herein. The crude EG is obtained from a process for the depolymerization of polyethylene terephthalate (PET) to form a terephthalate, including:

(i) admixing the polyethylene terephthalate (PET) with a first solvent that is methanol to yield a first mixture;

(ii) adding a glycoxide to the first mixture;

(iii) adding a second solvent that is methanol;

(iv) admixing; and (v) evaporating or distilling crude ethylene glycol from the terephthalate.

The crude ethylene glycol was fed into a first distillation column. The process column information for this Example is indicated in Table 2. The condensers utilized are a high efficiency inverted bell with jacketed wall design and containing water as the heat transfer medium.

TABLE 2

| Distillation Column Information for Example 1 | | | | |
|---|---|---|---|---|
| Column No. | 1 | 2 | 3 | Units |
| Column Diameter | 2 | 2 | 2 | in |
| No. of Trays | 13 | 13 | 8 | |
| No. of Stages | 15 | 15 | 10 | |
| Feed Tray Location | 10 | 10 | 8 | |
| Pressure | 110 | 110 | 100 | mm Hg |
| Feed Temperature | 40 | 130 | 152 | C. |
| Temperature | <56 | <197 | ≤197 to >202 | C. |
| Column Feed Flow Rate | .2 | .2 | .2 | L/min |
| Distilled gaseous stream flow rate | 0.16 | 0.16 | 0.19 | L/min |
| Extracted liquid stream flow rate | 0.04 | 0.04 | 0.01 | L/min |
| Condenser Temperature | 20 | 20 | 20 | C. |
| Reboiler Temperature | 50 | 50 | 130 | C. |

During operation, the second distillation column and the third distillation column operated at total reflux until the respective column was fully operational. Once fully operational, the reflux ratio was reduced to 0.16 L/min for the first distillation column and 0.19 L/min for the second distillation column. The column conditions were regulated by controlling reflux as a variable control. At the conclusion of the process, the purified ethylene glycol stream distilled in the third distillation column and after exiting the third condenser was evaluated and determined to contain 99.9 wt % ethylene glycol as shown in Table 3. The other constituent components in the purified ethylene glycol are also listed in Table 3.

TABLE 3

| | |
|---|---|
| Ethylene Glycol | 99.99% |
| 2-methoxyethanol | 41 |
| 1-butanol | 8 |
| neopentyl glycol | 0 |
| 2-(2-methoxyethoxy)-Ethanol | 0 |

TABLE 3-continued

| | |
|---|---|
| Tritan Monomer (1,3-cyclobutanediol 2,2,4,4-tetramethyl | 0 |
| Phenol | 0 |
| Acetone | 10 |
| Acetic acid, methyl ester | 1 |
| Ethanol | 22 |
| Propanoic acid, 3-methoxy-, methyl ester | 2 |
| Hexanoic acid, 2-ethyl-, methyl ester | 2 |
| Styrene | 1 |
| Propanoic acid, 2-hydroxy-methyl ester | 0 |
| Acetaldehyde, hydroxy | 0 |
| Acetic acid, hydroxy-, methyl ester | 0 |
| 1-Hexanol, 2-ethyl- | 0 |
| 1-Octanol | 0 |
| Cyclohexanemethanol, 4-methylene | 0 |
| (4-Methyl-cyclohex-3-enyl)-methanol | 0 |
| DMT | 0 |
| 9-Octadecenoic acid, methy ester | 0 |

Example 2

The crude EG used in the crude EG feed stream was produced in accordance with the process contained in U.S. Patent Publication No. 2019/0390035 titled "Terephthalic Acid Esters Formation" and incorporated herein. The crude EG is obtained from a process for the depolymerization of polyethylene terephthalate (PET) to form a terephthalate, including:

(i) admixing the polyethylene terephthalate (PET) with a first solvent that is methanol to yield a first mixture;

(ii) adding a glycoxide to the first mixture;

(iii) adding a second solvent that is methanol;

(iv) admixing; and (v) evaporating or distilling crude ethylene glycol from the terephthalate.

The components of the crude EG feed stream is listed in Table 1a and 1b above. The process column information for this Example is indicated in Table 4 the condenser information is indicated in Table 5 and the reboiler information is indicated in Table 6

TABLE 4

Distillation Column Information for Example 2

| | Column | | | |
|---|---|---|---|---|
| | First Distillation Column | Second Distillation Column | Third Distillation Column | Units |
| Column Feed Flow Rate | 14,248 | 1,980 | 1,891 | Kg/hr |
| # of Stages | 20 | 15 | 20 | |
| # of Trays | 18 | 13 | 18 | |
| Feed Tray Location | 9.15 | 5 | 5 | |
| Column Diameter | 1.28 | 0.56 | 1.13 | M |
| Pressure Drop Per Stage | 0.2 | 0.8 | 1 | torr/stage |

TABLE 5

Condenser Information for Example 2

| | Condenser | | | |
|---|---|---|---|---|
| | First Partial Condenser | Second Partial Condenser | Third Partial Condenser | Units |
| Temperature | 146 | 152 | 172 | C. |
| Heat Duty | −2.57 | −1.19 | −3.99 | MMBTU/h |
| Distillation Rate | 12,268 | 113 | 1,494 | kg/hr |
| Reflux Rate | 2,454 | 1,129 | 4,482 | kg/hr |
| Reflux Ratio | 0.20 | 10.00 | 3.00 | |
| Distillation to Feed Ratio | 0.86 | 0.06 | 0.80 | |
| Pressure | 562.546262 | 150 | 100 | Torr |

TABLE 6

Reboiler Information for Example 2

| | Reboiler | | | |
|---|---|---|---|---|
| | First Reboiler | Second Reboiler | Third Reboiler | Units |
| Temperature | 155 | 152.37 | 172.77 | C. |
| Heavy Duty | 8.44 | 1.34 | 5.28 | MMBTU/h |
| Bottoms Rate | 1,980 | 1,868 | 374 | kg/hr |
| Boilup Rate | 5,523 | 1,532 | 6,268 | kg/hr |
| Boilup Ratio | 2.79 | 0.82 | 17 | |
| Bottoms to Fee Ratio | 0.14 | 0.94 | 0.2 | |

The components in the various streams, with the streams corresponding to reference numerals shown in FIG. 1, are set forth in Table 7.

TABLE 7

Stream Components for Example 2

| Component | 12 ppm | 22 ppm | 32 ppm | 42 ppm | 52 ppm | 62 ppm | 72 ppm |
|---|---|---|---|---|---|---|---|
| Methanol | 860,554 | 998,761 | 4,466 | 99,248 | 0 | 0 | 0 |
| Ethylene Glycol | 111,494 | 0 | 802,112 | 98,670 | 835,259 | 999,333 | 178,961 |
| Diethylene Glycol | 6,181 | 0 | 44,471 | 0 | 46,566 | 0 | 232,830 |
| CHDM | 2,289 | 0 | 16,467 | 0 | 17,243 | 0 | 86,215 |
| Water | 5,838 | 1,234 | 34,358 | 763,507 | 0 | 0 | 0 |
| Triethylene Glycol | 26 | 0 | 187 | 0 | 195 | 0 | 977 |

TABLE 7-continued

| | | | Stream Components for Example 2 | | | |
| Component | 12 ppm | 22 ppm | 32 ppm | 42 ppm | 52 ppm | 62 ppm | 72 ppm |
|---|---|---|---|---|---|---|---|
| Dimethyl Terephthalate | 18 | 0 | 126 | 0 | 132 | 0 | 661 |
| Dimethyl Isophthalate | 82 | 0 | 590 | 1 | 618 | 3 | 3,076 |
| BHET/BHEI | 2,979 | 0 | 21,430 | 0 | 22,440 | 0 | 112,199 |
| Methyl 4-formylbenzoate | 291 | 0 | 2,093 | 6 | 2,191 | 29 | 10,841 |
| NaMMT | 661 | 0 | 4,756 | 0 | 4,980 | 0 | 24,901 |
| PET coloring | 8,706 | 0 | 62,631 | 0 | 65,582 | 0 | 327,911 |
| 2-Methoxyethanol | 199 | 0 | 1,432 | 31,823 | 0 | 0 | 0 |
| 1,4-Dioxane | 1 | 1 | 2 | 52 | 0 | 0 | 0 |
| 2-Methyl-1,3-Dioxolane | 1 | 2 | 0 | 1 | 0 | 0 | 0 |
| Sodium Sulfate | 22 | 0 | 161 | 0 | 169 | 0 | 845 |
| 1,4-Butanediol | 22 | 0 | 158 | 0 | 165 | 0 | 825 |
| 1,2-Propylene Glycol | 12 | 0 | 88 | 1 | 92 | 13 | 409 |
| Neopentyl Glycol | 327 | 0 | 2,355 | 4 | 2,465 | 66 | 12,065 |
| 1,5-Hexanediol | 4 | 0 | 30 | 0 | 32 | 0 | 159 |
| 2,3-Butanediol | 8 | 0 | 60 | 2 | 63 | 64 | 61 |
| 2,2-Dimethyl-1,3-Butanediol | 4 | 0 | 25 | 0 | 26 | 1 | 129 |
| 1,3-Cyclobutanediol 2,2,4,4-tetramethyl | 180 | 0 | 1,294 | 3 | 1,355 | 44 | 6,600 |
| Acetic Acid, hydroxy, ethyl ester | 2 | 0 | 18 | 389 | 0 | 0 | 0 |
| Diethyl Phthalate | 2 | 0 | 12 | 0 | 13 | 0 | 64 |
| Ethane 1,1'-oxybis[2-methoxy | 17 | 0 | 121 | 2,686 | 0 | 1 | 0 |
| 2-Butoxyethanol | 3 | 0 | 23 | 503 | 0 | 0 | 0 |
| 1-Propanol, 2-Ethoxy | 2 | 0 | 15 | 332 | 0 | 0 | 0 |
| 2-(2-Methoxyethoxy)-Ethanol | 52 | 0 | 372 | 13 | 389 | 437 | 197 |
| Ethanedioic Acid, Dimethylester | 17 | 0 | 122 | 2,539 | 8 | 10 | 0 |
| 1-Ethoxy-1Methoxy-Ethane | 3 | 2 | 10 | 221 | 0 | 0 | 0 |
| 2-Decanol | 2 | 0 | 15 | 0 | 16 | 1 | 74 |

As shown in Table 6, the purified ethylene glycol in stream 62 of Example 2 has a 99.9 wt % purity, resulting in a polyester-grade ethylene glycol.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A process for purifying polyester-grade ethylene glycol from crude ethylene glycol containing at least a first component and a second component that have a boiling point below that of ethylene glycol, comprising:

(a) providing a stream of crude ethylene glycol by depolymerizing polyethylene terephthalate in a chemical recycling process;

(b) introducing the crude ethylene glycol stream into a first distillation column for distilling the first component and removing the first component from the process, wherein a portion of a tail stream from the first distillation column is introduced into a first reboiler to provide heat energy to vaporize a portion of the tail stream for reintroduction into the first distillation column;

(c) withdrawing a first stream from a bottom of the first distillation column and feeding the first stream into a second distillation column for distilling the second component and removing the second component from the process, wherein a portion of a tail stream from the second distillation column is introduced into a second reboiler to provide heat energy to vaporize a portion of the tail stream for reintroduction into the second distillation column;

(d) withdrawing a second stream from a bottom of the second distillation column and feeding the second stream into a third distillation column, wherein a portion of a tail stream from the third distillation column is introduced into a third reboiler to provide heat energy to vaporize a portion of the tail stream for reintroduction into the third distillation column; and

17

(e) recovering polyester-grade ethylene glycol from top of the third distillation column, wherein the purity of the polyester-grade ethylene glycol is at least 99.9%.

2. The process for purifying polyester-grade ethylene glycol from crude ethylene glycol according to claim 1, wherein the first component is methanol.

3. The process for purifying polyester-grade ethylene glycol from crude ethylene glycol according to claim 1, wherein the second component is water.

4. The process for purifying polyester-grade ethylene glycol from crude ethylene glycol according to claim 2, wherein the purity of the methanol is 99.9%.

5. The process for purifying polyester-grade ethylene glycol from crude ethylene glycol according to claim 1, wherein the polyester-grade ethylene glycol contains less than 0.01 wt % chain terminators.

6. The process for purifying polyester-grade ethylene glycol from crude ethylene glycol according to claim 1, wherein the first distillation column, second distillation column, and third distillation column each comprise a partial condenser.

7. The process for purifying polyester-grade ethylene glycol from crude ethylene glycol according to claim 1, wherein the first distillation column operates at a temperature of less than 56° C. at a pressure of 110 mm Hg.

8. The process for purifying polyester-grade ethylene glycol from crude ethylene glycol according to claim 1, wherein the second distillation column operates at a temperature range of greater than 56° C. to 196° C., and a pressure of 110 mm Hg.

9. The process for purifying polyester-grade ethylene glycol from crude ethylene glycol according to claim 1, wherein the third distillation column operates at a temperature range of greater or equal to 197° C. to less than 202° C., and a pressure of 110 mm Hg.

10. The process for purifying polyester-grade ethylene glycol from crude ethylene glycol according to claim 1, wherein no catalysts or other additional components are introduced into the process of steps (b) through (d).

11. A process for purifying polyester-grade ethylene glycol from crude ethylene glycol, comprising:

(a) providing crude ethylene glycol from a process for the depolymerization of polyethylene terephthalate (PET) to form a terephthalate, comprising:

(i) admixing the polyethylene terephthalate (PET) with a first solvent that is methanol to yield a first mixture;

(ii) adding a glycoxide to the first mixture;

(iii) adding a second solvent that is methanol;

(iv) admixing; and (v) evaporating or distilling crude ethylene glycol from the terephthalate;

(b) introducing the crude ethylene glycol stream into a first distillation column for distilling a first component and removing the first component from the process, wherein a portion of a tail stream from the first distillation column is introduced into a first reboiler to provide heat energy to vaporize a portion of the tail stream for reintroduction into the first distillation column;

(c) withdrawing a first stream from a bottom of the first distillation column and feeding the first stream into a second distillation column for distilling a second component and removing the second component from the process, wherein a portion of a tail stream from the second distillation column is introduced into a second reboiler to provide heat energy to vaporize a portion of the tail stream for reintroduction into the second distillation column;

(d) withdrawing a second stream from a bottom of the second distillation column and feeding the second stream into a third distillation column, wherein a portion of a tail stream from the third distillation column is introduced into a third reboiler to provide heat energy to vaporize a portion of the tail stream for reintroduction into the third distillation column; and (e) recovering polyester-grade ethylene glycol from top of the third distillation column, wherein the purity of the polyester-grade ethylene glycol is at least 99.9%.

12. The process for purifying polyester-grade ethylene glycol from crude ethylene glycol according to claim 11, wherein the crude ethylene glycol contains one or more of the following methanol, ethylene glycol, water, diethylene glycol, CHDM, BHET, BHEI, Methyl 4-formylbenzoate, pigments and dyes, 2-Methoxyethanol, 2-Butoxyethanol, and 2-(2-Methoxyethoxy)-Ethanol.

13. The process for purifying polyester-grade ethylene glycol from crude ethylene glycol according to claim 11, wherein the first component is methanol.

14. The process for purifying polyester-grade ethylene glycol from crude ethylene glycol according to claim 11, wherein the second component is water.

15. The process for purifying polyester-grade ethylene glycol from crude ethylene glycol according to claim 11, wherein no catalysts or additional components are introduced into the process of steps (b) through (d).

\* \* \* \* \*